United States Patent [19]

Clausen et al.

[11] Patent Number: 5,030,241
[45] Date of Patent: Jul. 9, 1991

[54] USE OF 2,6-DINITRO-ANILINE DERIVATIVES IN HAIR DYES AND NEW 2,6-DINITRO-ANILINE DERIVATIVES

[75] Inventors: Thomas Clausen, Alsbach; Eugen Konrad, Darmstadt, both of Fed. Rep. of Germany

[73] Assignee: Wella Aktiengesellschaft, Darmstadt, Fed. Rep. of Germany

[21] Appl. No.: 283,948

[22] PCT Filed: Mar. 29, 1988

[86] PCT No.: PCT/EP88/00260

§ 371 Date: Nov. 21, 1989

§ 102(e) Date: Nov. 21, 1989

[87] PCT Pub. No.: WO88/08696

PCT Pub. Date: Nov. 17, 1988

[30] Foreign Application Priority Data

May 4, 1987 [DE] Fed. Rep. of Germany ....... 3714775

[51] Int. Cl.$^5$ .................. A61K 7/13; C07C 211/52
[52] U.S. Cl. ............................. 8/414; 8/409; 564/441
[58] Field of Search .............. 8/414; 564/441, 442, 564/443

[56] References Cited

U.S. PATENT DOCUMENTS

| | | | |
|---|---|---|---|
| 2,750,326 | 6/1956 | Eckardt et al. | 8/414 |
| 3,488,138 | 1/1970 | Isowitz | 8/414 |
| 3,654,363 | 4/1972 | Pum et al. | 564/441 |
| 3,699,167 | 10/1972 | Kaiser | 564/441 |
| 3,930,792 | 1/1976 | Alperin et al. | 8/414 |
| 4,395,577 | 7/1983 | Maulding | 568/936 |
| 4,808,190 | 2/1989 | Grollier et al. | 8/406 |
| 4,835,314 | 5/1989 | Konrad et al. | 8/414 |

FOREIGN PATENT DOCUMENTS 1511025 1/1968 France .
1116138 6/1968 United Kingdom .
2090853 7/1982 United Kingdom .
2168369 6/1986 United Kingdom .

OTHER PUBLICATIONS

Corbett, John F., The Chemistry of Hair-Color Products, *JSDC*, pp. 285–303, Aug. 1976.
Zviak, The Science of Hair Care, Marcel Dekker Inc., ISB10 0-8247-7378-0, pp. 235–286.

*Primary Examiner*—Paul Lieberman
*Assistant Examiner*—J. E. Darland
*Attorney, Agent, or Firm*—Michael J. Striker

[57] ABSTRACT

The method of dyeing hair comprises applying to the hair a dye containing a 2,6-dinitro-aniline derivative having the general formula (I)

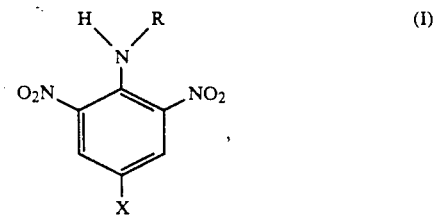

wherein R represents H, $C_1$–$C_4$ alkyl, $C_2$–$C_4$ monohydroxy alkyl or $C_3$–$C_4$-dihydroxy alkyl and X represents one of the radicals $C_1$–$C_4$ alkyl, $C_2$–$C_4$ monohydroxy alkyl, $C_1$–$C_4$ perfluoro alkyl, $C_1$–$C_4$ alkoxy, $C_2$–$C_4$ monohydroxy alkoxy, $C_3$–$C_4$ dihydroxy alkoxy or halogen. The present invention also comprises hair dyes containing at least one compound having the formula (I) and novel 2,6-dinitro-aniline derivatives. The dyes having the formula (I) have good physiological properties and provide all the yellow shades required for dyeing from a bluish-tinged lemon-yellow via a pure yellow to red-orange.

23 Claims, No Drawings

USE OF 2,6-DINITRO-ANILINE DERIVATIVES IN HAIR DYES AND NEW 2,6-DINITRO-ANILINE DERIVATIVES

BACKGROUND OF THE INVENTION

The present invention relates to nitro dyes for dyeing hair and, more specifically, to 2,6-dinitro-aniline derivatives used as nitro dyes, as well as to the use of compositions containing 2,6-dinitro-aniline derivatives and to the novel 2.6-dinitro-aniline derivatives.

The use of nitro dyes in hair dyes is widespread today. They are used in oxidation hair dyes as additives for producing natural or modern shades. However, by combining several differently colored nitro dyes it is also possible to produce hair dyes which are capable of dyeing hair in natural to modern shades without the use of oxidizing agents.

Thus, brown colours having a natural effect can be produced by combining, for example, an orange-dyeing nitro dye with a blue-dyeing one. However, in addition, it is also possible to obtain a similar result with a yellow-dyeing and a violet-dyeing nitro dye. Therefore, either yellow nitro dyes which can dye the hair in an intense pure lemon-yellow colour, that must be as free from red components as possible, or those which dye the hair orange and can be applied in combination with pure blue dyes are required.

Furthermore, hair dyes must satisfy many additional requirements. The nitro dyes must be harmless in toxicological and dermatological respects. For their use in oxidation dyes it is a prerequisite that they are stable in the presence of hydrogen peroxide in alkaline solution. Furthermore, a good light fastness, resistance to acid and rubbing fastness are required for the hair colorations produced. Finally, it should be possible to produce the nitro dyes by a simple process.

The substituted amino-nitrophenols described in their literature heretofore for dyeing the hair yellow satisfy the above-mentioned requirements only to a limited extent. It is true, the 4-nitro-3-(2'-hydroxy-ethyl)aminophenol described in *International Journal of Cosmetic Science* 1982, Page 25 to 35, does produce a lemon-yellow coloration. However, this coloration has a very low color intensity. Two further isomers, namely, the 4-nitro and the 5-nitro-2(2'-hydroxy-ethyl)aminophenol are pH-sensitive due to the aromatic hydroxy groups and show undesirable colour changes when exposed to the action of acid or alkali.

The o-, m- and p-nitro-aniline derivatives mentioned in DE-AS 1619395 are further known nitro dyes. In fact these compounds substantially satisfy the requirements with regard to the application technology but they are not satisfactory with regard to physiological properties.

The 2-nitro-aniline derivatives described in DE-OS 3 442 757 do satisfy the requirements to a great extent but the color scale attainable by varying the substituents cannot be extended into the red range. Therefore, no modern reddish hair colors can be produced with the 2-nitro-aniline derivatives described therein without the additional application of red dyes.

SUMMARY OF THE INVENTION

Accordingly, it is an object of the present invention to provide nitro-aniline derivatives having the advantageous properties of the compounds according to DE-OS 3 442 757 and, in addition, an extension of the color scale into the red range (by variation of the substituents).

This object and others which will become apparent hereinafter are attained in a 2,6-dinitro derivative having the general formula (I).

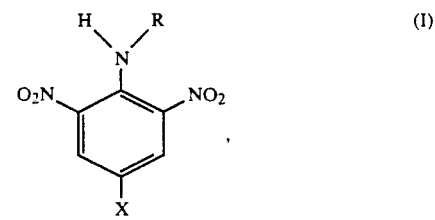

wherein R represents H, $C_1$–$C_4$ alkyl, $C_2$–$C_4$ monohydroxy-alkyl or $C_3$–$C_4$ dihydroxy-alkyl and X represents one of the radicals $C_1$–$C_4$ alkyl, $C_2$–$C_4$ monohydroxy alkyl, $C_1$–$C_4$ perfluoro alkyl, $C_1$–$C_4$ alkoxy, $C_2$–$C_4$ monohydroxy alkoxy, $C_3 1 \propto C_4$ dihydroxy alkoxy or halogen. As a dye in hair dyes this 2,6-dinitro-analine derivative achieves this in an excellent manner.

By varying the radical X there are available compounds having the formula (I) which now yield all the shades required from a bluish-tinged lemon yellow via a pure yellow and orange to a red orange.

As compared with the dyes of the 2-nitro-aniline type according to DE-OS 3 442 757, with the compounds having the general formula (I) the color scale can be extended into the red range. Not only is it thus possible, by combining these dyes with suitable blue or violet dyes to produce brown colourations having a natural effect, but modern reddish hair colors can also be produced without the additional application of red dyes.

Among the compounds covered by the formula (I) the use of 2,6-dinitro-aniline derivatives having the general formula (I), wherein R represents 2-hydroxy-ethyl or 2,3-dihydroxy propyl and X represents one of the radicals $CH_3$, $CF_3$, $CH_2OH$, $OCH_3$, $OCH_2CH_2OH$, $OCH_2CH(OH)CH_2OH$, Cl or Br is preferred as a dye in hair dyes for dyeing and physiological reasons.

Examples of 2,6-dinitro-aniline derivatives having the general Formula (I), which are suitable according to the present invention are 2,6-dinitro-4-methyl-(2'-hydroxy-ethyl)aniline, 2,6-dinitro-4-methyl-(2',3'-dihydroxy-propyl)aniline, 2,6-dinitro-4-trifluoromethyl-(2',3'-dihydroxy-prophl)aniline, 2,6-dinitro-4-trifluoromethyl-(2'-hydroxy-ethyl)aniline, 2,6-dinitro-4-methoxy-(2'-hydroxy-ethyl)aniline, 2,6-dinitro-4-methoxy-(2',3'-dihydroxy-propyl)aniline, 2,6-dinitro-4-(2'-hydroxy-ethyl-oxy)-(2'',3''-dihydroxy-propyl)aniline, 2,6-dinitro-4-(2'-hydroxy-ethyloxy)-2''-hydroxy-ethyl)aniline and 4-chloro-2,6-dinitro-(2', 3'-dihydroxy-propyl)aniline.

The very good toxicological and physiological properties of the compounds having the general formula (I) are surprising. Thus, all the dyes tested, for example, those in which R represents a hydroxy-ethyl group or a dihydroxy-propyl group and X represents one of the radicals methyl, trifluoromethyl or methoxy, are not mutagenic. Therefore, and for solubility reasons and because of the depth of color they are particularly preferred also as compared with one non-hydroxy-alkylated nitro-aniline derivatives.

The compounds having the general formula (I) are nitro dyes which dye yellow to red-orange and are outstandingly suitable for dyeing human hair. They are readily soluble in water and have an excellent storage life.

Therefore, the present invention also provides a composition for dyeing hair which contains a dye and cosmetic additives conventionally used in hair dyes. This a composition is characterized in that it contains a 2-6, dinitro-aniline derivative having the general formula (I), preferably in an amount of 0.01 to 2.0 percent by weight. Of this a composition the one containing a 2,6-dinitro-aniline derivative having the formula (I), wherein R represents (2-hydroxy-ethyl or 2,3-dihydroxy-propyl and X has the meaning defined in formula (I), is preferred.

The composition according to the present invention for dyeing hair relates to an embodiment in which it is applied without adding an oxidizing agent as well as to a further embodiment in which the addition of an oxidizing agent is required.

The hair dye initially mentioned, i.e., that without the addition of an oxidizing agent, is an agent which can also contain other conventional direct hair dyes in addition to the dyes having the formula (I). Among the dyes known for hair dyeing the following dyes are mentioned: aromatic nitro dyes, as for example 2-amino-4-nitro-phenol, picramic acid, 1-(2'-hydroxy-ethyl)amine-2amino-4-nitro-benzene, 4-(2'-ureido-ethyl)-amino-nitro-benzene, 4-(2',3'-dihydroxy-propyl)amino-3-nitro-trifluoromethyl benzene, 4-(2'-hydroxy-ethyl)amino-3-nitro-toluene, 1,4-bis(2'-hydroxy-ethyl)amino-4-N-ethyl-2-nitro-benzene, 2-nitro-4-(2'-hydroxy-ethyl)amino-aniline, 4-bis(2'-hydroxy-ethyl)amino-1-methyl-amino-2-nitro benzene, 2,5-bis(2'-hydroxy-ethyl)amino-nitro-benzene, 2-(2'-hydroxy-ethyl)amino-4,6-dinitro-phenol, 1-amino-4-(2',3'-dihydroxy-propyl)amino-2-nitro-5-chloro benzene. 4-bis(2'-hydroxy-ethyl)amino-2-nitro-benzene and 1-amino-2-nitro-4-bis(2'-hydroxy-ethyl)amino-benzene; triphenyl methane dyes, as for example, Basic Violet 1 (C.I. 42535); Azo Dyes, as for example, Acid Brown 4 (C.I. 14805); Anthraquinone Dyes, as for example Disperse Blue 23 (C.I. 61545), Disperse violet 4 (C.I. 61105), 1,4,5,8-tetramine-anthraquinone and 1,4-diamine-anthraquinone. Depending on the type of their substituents the dyes of these classes can have an acid, non-inorganic or basic character. Further suitable direct hair dyes are described, for example, in the book by J. C. Johnson, *Hair Dyes* Noyes Data Corp. Park-Ridge (U.S.A.) (1973), Page 3 to 91 and 113 to 139 (ISBN: 0-8155-0477-2).

The form of preparation of the hair dye described here, which is based on direct hair dyes, can be, for example, a solution, particularly an aqueous or aqueous-alcoholic solution. Furthermore, preferred forms of preparation are a cream, a gel or an emulsion and they can also be sprayed in a mixture with a propellant or by means of a pump. The dyes having the general formula (I) are to be contained in this hair dye with no oxidizing agent added in a concentration of approximately 0.01 to 2 percent by weight, preferably 0.01 to 1.0 percent by weight. The total content of the direct hair dyes is within the limits of approximately 0.01 to 3.0 percent by weight.

The pH value of this hair dye lies in the range of 3 to 10.5, particularly at pH 7.5 to 9.5, the adjustment of the desired alkaline pH value primarily being carried out with ammonia, but it can also be carried out with organic amines, as for example, monoethanol-amine or triethanol-amine.

Its application is carried out in the conventional manner by applying the composition to the hair in an amount adequate for dyeing the hair. It remains in contact with the hair for a period of approximately 5 to 30 minutes. The hair is subsequently rinsed with water and, when required, also with the aqueous solution of a weak organic acid, and then dried. For example, acetic acid, citric acid, tartar acid and the like can be used as the weak organic acid. The above-descried hair dye without the addition of an oxidizing agent can of course also contain cosmetic polymers so that a fixation of the hair is simultaneously attained with the dyeing. These agents are usually referred to as shade fixatives or dye fixatives.

Among the polymers known for this purpose in cosmetics the following polymers are mentioned here, for example, polyvinyl pyrrolidone, polyvinyl acetate, polyvinyl alcohol or polyacrylic basic polymers of esters of these two acids and amino alcohols and their salts or quaternary products, polyacrylonitrile, polyvinyl lactams and copolymers of these compounds, as for example, polyvinyl pyrolidone-vinyl acetate and the like.

Natural polymers, such as chitosan (deacetylated chitin) or chitosan derivatives can also be use for said purpose.

The polymers are contained in this composition in the amount normally used for these compositions, namely, from approximately 1 to 5 percent by weight. The pH value of this composition ranges from approximately 6.0 to 9.0.

The application of this hair dye with additional fixation is carried out in the conventional manner by moistening the hair with setting lotion, laying the hair in the desired style and by subsequent drying.

Of course, when required, the above-described hair dye without an added oxidizing agent can contain further additives conventionally used in hair dyes, as for example, care agents, wetting agents, thickeners, softeners, preservatives and perfume oils as well as other additives which are used for oxidation hair dyes and are listed below.

As initially mentioned the present invention also relates to a hair dye in which the addition of an oxidizing agent is required. Apart from the dyes according to the defined formula (I) and, when required, direct hair dyes, it also contains additional conventional hair dyes requiring an oxidative development.

These oxidation dyes are primarily aromatic p-diamines and p-aminophenols, as for example, p-tolylene diamine, p-phenylene diamine, p-aminophenol and similar compounds, which are combined with so-called modifiers, as for example, m-phenylene diamine, resorcinol, m-aminophenol, etc., for the purpose of varying the colorations.

These types of oxidation dyes know and customary for hair dyeing are described in the book by E. Sagarin, *Cosmetics, Science and Technology* (1957) Interscience Publishers Inc. New York, Page 503 ff. and in the book by H. Janlstyn, *Handbuch der Kosmetika und Riechstoffe* (1973), Page 338 ff.

With mixtures of these oxidation dyes and the dyes according to the formula (I) natural blond and brown shades as well as modern nuances can be very easily produced.

The dyes according to the formula (I) are contained in this hair dye (with the addition of oxidizing agent) in a concentration of approximately 0.01 to 2.0 percent by weight, preferably 0.01 to 1.0 percent by weight. The total content of dyes in this hair dye is approximately 0.1 to 5.0 percent by weight.

Oxidation hair dyes are usually adjusted to be alkaline, preferably to pH values of approximately 8.0 to 11.5, the adjustment being carried out particularly with ammonia. However, other organic amines, for example, monoethanol amine or triethanol amine, can also be used for this purpose. Primarily hydrogen peroxide and its addition compounds are suitable as oxidizing agents for the development of the hair colorations. The form of preparation of this hair dye can be the same as for the hair dye without the addition of an oxidizing agent, but the preparation is preferably in the form of a cream or gel.

Conventional additives in creams, emulsions or gels are, for example, solvents such as water, low aliphatic alcohols, for example, ethanol, propanol, isopropanol, glycerol or glycols, as for example, ethylene glycol and propylene glycol or even glycol ether, furthermore, wetting agents and emulsifiers from the classes of the anionic, cationic, amphoteric or non-Ionogenic surface-active substances, as for example, fat alcohol sulphates, fat alcohol ether sulphates, alkyl sulphonates, alkyl benzene sulphates, alkyl-trimethyl ammonium salts, alkyl betaines, oxethylated fat alcohols, oxethylated nonyl phenols, fatty acid alkanol amides, oxethylated fatty esters, furthermore, thickeners, as for example, higher fat alcohols, bentonite, starch, polyacrylic acid, cellulose derivatives, as for example, carboxymethyl cellulose, alginates, vaseline, paraffin oil, and fatty acids as well as care agents, as for example, lanolin derivatives, cholesterol, panthothenic acid and betaine and also perfume oils and complexing agents. The above-mentioned ingredients are applied in the amounts customary for these purposes, for example, the wetting agents and emulsifiers in concentrations of approximately 0.5 to 30 percent by weight while the thickeners can be contained in the preparations in an amount of approximately 0.1 to 2.5 percent by weight and the care agents in an amount of approximately 0.1 to 5 percent by weight.

The application of the preparations for which the addition of an oxidizing agent is required is carried out in a conventional manner in that prior to the treatment the hair dyes are mixed with the oxidizing agent and/or an amount of the mixture adequate for dyeing the hair, usually about 50 to 150 ml, is applied to the hair. After a reaction time adequate for dyeing the hair—usually about 10 to 45 minutes—the hair is rinsed with water, when required, subsequently with the aqueous solution of a weak organic acid, as for example, citric acid or tartaric acid, and then dried.

With regard to the dyeing possibilities the hair dyes according to the present invention provide a broad scale of different color shades extending from natural shades to ultramodern bright shades, depending on the colour components. Depending on their composition the dyes are applied either in combination with hydrogen peroxide or also without an oxidizing agent.

Some of the 2,6-dinitro-aniline derivatives having the formula (I) are known. Thus, for example, the production for the following compounds is described in the literatures:

| Substituent | | Literature |
|---|---|---|
| X | R | |
| CH$_3$ | H | W. Staedel, Liebigs Ann. Chem. 217, |

-continued

| Substituent | | Literature |
|---|---|---|
| X | R | |
| | | 186 (1883) |
| CH$_3$ | CH$_3$ | L. Gattermann, Ber. Dtsch. Chem. Ges. 18, 1487 (1885) |
| CH$_3$ | C$_2$H$_4$OH | DE-OS 32 00 787 |
| CH$_3$ | OH<br>CH$_2$CHCH$_2$OH | DE-OS 32 00 787 |
| CH$_3$ | C$_2$H$_5$ | L. Gattermann, Ber. Dtsch. Chem. Ges. 18, 1485 (1885) |
| CH$_3$ | C$_3$H$_7$ | A. Hantzsch, Ber. Dtsch. Chem. Ges. 43, 1673 (1910) |
| CH$_3$ | C$_4$H$_9$ | J. Reilly and W. J. Hickinbottom J. Chem. Soc. (London) 113, 990 (1918) |
| CF$_3$ | H | C. M. Jagupolskii and V. S. Mospan, Ukr. Chim. Z. 21, 81, 83 (1955), C.A. 49, 8866 (1955) |
| CF$_3$ | C$_2$H$_4$OH | B. F. Malichenko, E. M. Levchenko and L. M. Yagupolskii. Ukr. Chim. Z. 33, 717–719 (1967), C.A. 68, 39228, (1968) |
| Cl | H | R. C. Elderfield, W. J. Gensler and O. Birstein, J. Org. Chem. 11.812.820 (1946) |
| Cl | C$_2$H$_4$OH | K. F. Waldkotter, Recueil Trav. Chimiques Pays-Bas 57, 1294, 1299, 1301 (1938) |
| Br | C$_2$H$_4$OH | |
| Cl | C$_2$H$_5$ | K. F. Waldkotter. Recueil Trav. Chimiques Pays-Bas 58, 132, 136 (1939) |
| Br | C$_2$H$_5$ | |
| Br | H | G. S. Hammond, F. J. Modic and R. M. Hedges. J. Am. Chem. Soc. 75, 1388, 1389 (1953) |
| OCH$_3$ | H | F. Reverdin, Ber. Dtsch. Chem. Ges. 42, 1524 (1909) |
| OC$_2$H$_5$ | H | F. Reverdin, Helv. Chimica Acta 12, 117, 119, 1058 (1929) |
| OC$_2$H$_5$ | CH$_3$ | F. Reverdin and F. Liebl, J. prakt. Chemie 2 86, 205 (1912) |
| OCH$_3$ | CH$_3$ | H. H. Hodgson and J. H. Crook, J. Chem. Soc. (London) 1933, 825, 827 |

The present invention also provides novel 2,6-dinitroaniline derivatives having the general formula (II)

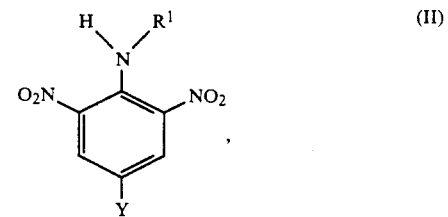

wherein R$^1$ represents C$_2$–C$_6$ monohydroxyl alkyl or C$_3$–C$_4$ dihydroxy alkyl and Y represents one of the radicals C$_2$–C$_4$ alkyl, C$_2$–C$_4$ monohydroxy alkyl, C$_1$–C$_4$ perfluoroalkyl, C$_1$–C$_4$ alkoxy, dihydroxy alkoxy or halogen, provided that, when Y represents chlorine or bromine, R$^1$ does not represent hydroxy ethyl and, when Y represents trifluoromethyl, R$^1$ does not represent monohydroxy alkyl.

Examples of novel 2,6-dinitro-aniline derivatives having the formula (II) are 2,6-dinitro-4-trifluoro-methyl-(2',3'-dihydroxy-propyl)aniline, 2,6-dinitro-4-methoxy-(2',3'-dihydroxy-propyl)aniline, 2,6-dinitro-4-methoxy-(2'-hydroxy-ethyl)aniline, 2,6-dinitro-4-(2'-hydroxy-ethyl-oxy)-2"-hydroxy-ethyl)aniline. 2,6-dinitro-4-(2'-hydroxy-ethyl-oxy)-2",3"-dihydroxy-propyl)aniline and 4-chloro-2,6-dinitro-(2′, 3′-dihydroxy-propyl)aniline.

The production of the compounds having the formula (II) is carried out by nucleophilic exchange of an alkoxy group or of a halogen atom (A) in the corresponding compound (III), substituted by Y, according to the reaction equation hereafter.

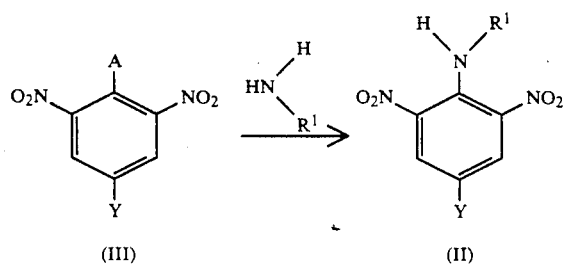

The production of the 2,6-nitro-aniline derivatives having the formula (I) and (II) can also be carried out by dinitration of the aniline derivatives protected, when required, for example, by a toluene-sulphonyl radical and substituted in the para position by X and Y. The 4-chloro- or 4-bromo-2,6-dinitro-aniline derivatives can be obtained by chlorination or bromination of the 2,6-dinitro aniline. Furthermore, the corresponding unsubstituted amino compounds can be reacted to the N-alkyl compounds by conventional alkylation processes.

The present invention will be further illustrated by the following Examples.

EXAMPLES

Example 1

2,6-dinitro-trifluoromethyl-(2′, 3′-dihydroxypropyl)analine 1 g of 4-chloro-3,5-dinitro-benzo trifluoride was dissolved in 4 ml of dimethyl sulphoxide, whereupon 1 ml of 2,3-dihydroxy-propyl amine was added dropwise while stirring. After the exothermic reaction had subsided the mixture was stirred for half an hour at room temperature and was then poured on ice. The precipitated crystals were filtered with suction. Upon drying, 1.0 g (83 percent of the theoretical yield) of the yellow dye having a melting point of 129° to 130° C. was obtained.

Mass Spectrum: 325 (M+, 14), 264(100), 247(10), 217(16), 160(16), 159(12), 61(18).

For this mass spectrum and all the subsequent mass spectra the following rule applies:

All the peaks whose intensity is greater than 10 percent are defined in m/e (relative intensity in percent).

UV Spectrum: 208(4.18) 234sh(3.99), 310(3.67), 350(3.70), 416(3.39).

For this UV spectrum and all the subsequent UV spectra the following rule applies:

Solvent: ethanol.

The peaks are characterized by defining the wave length of the maximum in nanometers (logarithmic extinction coefficient).

Example 2

2,6-dinitro-4-methoxy-(2′-hydroxy-ethyl)aniline 1 g of 2,6-dinitro-hydroquinone dimethyl ether (B. Relchert and W. Turkewitsch, *Arch. der Pharmazie* 276, 397, 406 (1938)) was stirred in 15 ml of ethanol amine for one hour at room temperature, whereupon the mixture was poured on ice and neutralized with acetic acid. The precipitated red crystals were filtered with suction. 0.9 g (78 percent of the theoretical yield) of the product was obtained; it has a melting point of 104° C.

1H-NMR Spectrum: 8.1 (broad, OH, NH, the signal disappears on shaking the sample with D20), 7.78 (s, 3—H, 5—H), 3.85 (s, OCH3), 3.84 (t, J=5Hz, HN—CH2CH2—OH), 3.13 (g, J=5 Hz, HN—CH2, on shaking the sample with D20 the signal forms a t,J=5 Hz), 1.68 (broad, OH, NH, on shaking the sample with D20 the signal disappears).

For this NMR spectrum and all the subsequent NMR spectra the following rule applies:

The chemical displacement is defined in delta (p.p.m.), the coupling constants are defined in Hertz.

Standard: tetramethyl silane.

Solvent: CDCI3 unless stated otherwise.

s=singlet, d=doublet, t=triplet, q=quartet, m=multiplet.

Example 3

2,6-dinitro-4-methoxy-(2′,3′-dihydroxy-propyl) aniline 1 g of 2,6-dinitro-hydroquinone dimethyl ether (see Example 2) was dissolved in 8 ml of dimethyl sulphoxide and mixed with 3.6 g of 1-amino-propanediol-2,3 while stirring. The mixture was then stirred for 3½ hours at room temperature, whereupon it was poured on ice and the red crystals were filtered with suction 0.95 g (74 percent of the theoretical yield) of the desired dye was obtained.

NMR Spectrum (in DMSO-d6): 8.02 (t, J=5 Hz, NH, the signal disappears on shaking the sample with D20), 7.89 (s, 3—H, 5—H), 5.13 (q, J=5 Hz, OH; the signal disappears on shaking the sample with D20), 4.65 (t, j=5 Hz, OH; the signal disappears on shaking the sample with D20). 3.82, (s, OCH3),

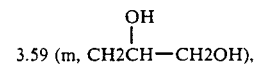

3.59 (m, CH2CH—CH2OH), 3.28 (m, —CH20H), 2.88 (m, HN—CH2).
UV Spectrum: 234 (4.37), 468 (3.74)

Example 4

4-chloro-2,6-dinitro-(2′,3′-dihydroxy-propyl)aniline 0.25 g of 4-chloro-2,6-dinitro-anisole (Kohn and Kramer, *Monatsh, Chemie* 49, 154) was dissolved in 2 ml of 2,3-dihydroxy-propylamine at 5° to 10° C. and stirred at this temperature for half an hour, whereupon the orange solution was pour on ice and the precipitated yellow crystals were filtered with suction. 0.2 g (64 Percent of the theoretical yield) of the dye was obtained, it had a melting of 82° C.

| Elementary Analysis (C9H10ClN2O5): | | |
|---|---|---|
| | computed: | obtained: |
| C % | 37.06 | 36.92 |
| H % | 3.45 | 3.49 |
| N % | 14.40 | 14.21 |

EXAMPLES OF HAIR DYE

Example 5

Liquid Hair Dye

| | | |
|---|---|---|
| 0.30 | g | of 2,6-dinitro-4-methyl-(2',3'-dihydroxy-propyl)anlline |
| 2.00 | g | of lauryl alcohol-diglycol ether sulphate-sodium salt (28% aqueous solution) |
| 2.00 | g | of 25% ammonia |
| 95.70 | g | of water |
| 100.0 | g. | |

Bleached natural hair was treated for 20 minutes with the solution according to Example 5 at room temperature, whereupon it was rinsed with water and then dried. The hair was dyed to a bright orange.

Example 6

Dye Fixative

| | | |
|---|---|---|
| 0.10 | g | of 2,6-dinitro-4-trifluoromethyl (2',3'-dihydroxy-propyl)aniline |
| 2.00 | g | of polyvinyl pyrrolidone |
| 0.10 | g | of glycerol |
| 40.0 | g | of isopropanol |
| 57.80 | g | of water |
| 100.00 | g. | |

White human hair was laid with the dye fixative and dried. The hair was dyed bright lemon yellow and fixed.

Example 7

Oxidation Hair Dye in Cream Form

| | | |
|---|---|---|
| 0.01 | g | of 2,6-dinitro-4-(2'-hydroxy-ethoxy)-(2'',3''-dihydroxy-propyl)aniline |
| 0.20 | g | of p-phenyline diamine |
| 0.15 | g | of resorcinol |
| 0.03 | g | of m-aminophenol |
| 15.00 | g | of cetyl alcohol |
| 3.50 | g | of lauryl alcohol-diglycol ether sulphate-sodium salt (28% aqueous solution) |
| 6.00 | g | of 25% ammonia |
| 75.02 | g | of water |
| 100.00 | g. | |

Shortly before its application 50 g of the above hair dye were mixed with 50 ml of a 6% hydrogen peroxide solution. The mixture was subsequently applied to gray human hair and allowed to react for 30 minutes at a temperature of 40° C.

Upon rinsing the hair with water water and subsequent drying it had assumed a modern reddish blond shade.

Example 8

Hair Dye in Cream Form

| | |
|---|---|
| 0.050 g | of 4-chloro-2,6-dinitro-(2',3'-dihydroxy-propyl)aniline |
| 0.250 g | of 4-bis(2'-hydroxy-ethyl)amino-1-methyl-amino-2-benzene |
| 0.020 g | of 1-amino-2-nitro-4-bis(2'-hydroxy-ethyl)amino-benzene |
| 0.025 g | of Disperse Blue 23 (C.I. 61 545) |
| 7.500 g | of cetyl alcohol |
| 1.750 g | of lauryl alcohol-diglycol ether sulphate-sodium salt (28% aqueous solution) |
| 0.100 g | of p-hydroxy benzoic methyl ester |
| 0.200 g | of 25% ammonia |
| 90.105 g | of water |
| 100.000 g. | |

1.750 g of lauryl alcohol-diglycol ether sulphate-sodium salt (28% aqueous solution) 0.100 g of p-hydroxy benzoic methyl ester 0.200 g of 25% ammonia 90.105 g of water 100.000 g.

50 g of the above hair dye were applied white human hair and rinsed with water after a reaction time of 20 minutes. The hair was then dried. It has been dyed a natural brown shade.

Example 9

Liquid Hair Dye

| | | |
|---|---|---|
| 0.25 | g | of 2,6-dinitro-4-methoxy-(2',3'-hydroxy-propyl)aniline |
| 0.10 | g | of 1-amino-4-(2',3'-dihydroxy-propyl)-amino-2-nitro-5-chloro benzene |
| 0.20 | g | of 4-bis(2'-hydroxy-ethyl)amino-1-methyl-amino-2-nitro-benzene |
| 0.50 | g | of hydroxy-ethyl cellulose |
| 5.00 | g | of lauryl alcohol-diglycol ether sulphate-sodium salt (28% aqueous solution) |
| 10.00 | g | of isopropanol |
| 10.00 | g | of 25% ammonia |
| 73.95 | g | of water |
| 100.00 | g. | |

Bleached natural hair was treated with the solution according to Example 9 for 20 minutes at room temperature. Upon rinsing the hair with water and subsequent drying the hair had been dyed a modern dark Beaujolais shade.

Example 10

Liquid Hair Dye

| | | |
|---|---|---|
| 0.30 | g | of 2,6-dinitro-(2'-hydroxy-ethyl-oxy)-(2''-hydroxy-ethyl)aniline |
| 0.05 | g | of 1,4-bis(2'-hydroxy-ethyl)amino-2-nitro-benzene |
| 0.50 | g | of hydroxy-ethyl cellulose |
| 5.00 | g | of lauryl alcohol-diglycol ether sulphate-sodium salt (28% aqueous solution) |
| 10.00 | g | of isopropanol |
| 10.00 | g | 25% ammonia |
| 74.15 | g | of water |
| 100.00 | g. | |

The above hair dye was allowed to act on a bleached natural hair for 30 minutes at 40° C. Upon rinsing with water and subsequent drying the hair had been dyed a modern blond shade.

It will be understood that each of the elements described above, or two or more together may also find a useful application in other types of compositions differing from those described above.

While our invention has been illustrated and described as embodied in a hair dye, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapted it for various applications without omitting features that, from the standpoint or prior art, fairly constitute essential characteristics of the generic or specific aspects of our present invention.

What is claimed as new and desired to be protected by Letters Patent is set forth in the appended claims.

The embodiments of the invention in which an exclusive property or privilege is claimed are defined as follows:

1. A method of dyeing hair which comprises applying thereto a hair dye containing a 2,6-dinitro-aniline derivative having the general formula (I)

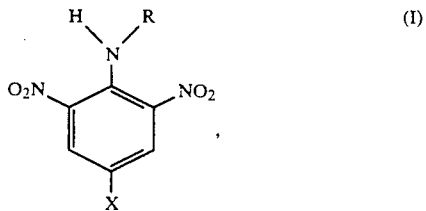

wherein R represents H, $C_1$-$C_4$ alkyl, $C_2$-$C_4$ monohydroxy alkyl or $C_3$-$C_4$ dihydroxy alkyl and X represents one of the radicals $C_1$-$C_4$ alkyl, $C_2$-$C_4$ monohydroxy alkyl, $C_1$-$C_4$ perfluoro alkyl, $C_1$-$C_4$ alkoxy, $C_2$-$C_4$ monohydroxy alkoxy, $C_3$-$C_4$ dihydroxy alkyl or halogen.

2. A method according to claim 1, wherein R represents 2-hydroxy ethyl or 2,3-dihydroxy propyl and X represents one of the radicals $CH_3$, $CF_3$, $CH_2OH$, $OCH_3$, $OCH_2CHOH$, $OCH_2CH(OH)CH_2OH$, Cl or Br.

3. A composition for dyeing hair containing 0.01 to 2.0 percent by weight of a 2,6-dinitro-aniline derivative having the formula (I)

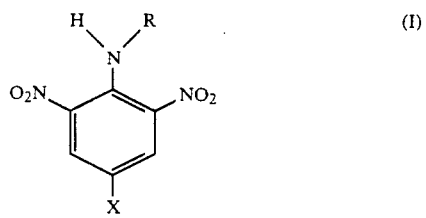

wherein R is selected from the group consisting of H, $C_1$-$C_4$ alkyl, $C_2$-$C_4$ monohydroxyalkyl and $C_3$-$C_4$ dihydroxyalkyl and X is selected from the group consisting of $C_1$-$C_4$ alkyl, $C_2$-$C_4$ monohydroxyalkyl, $C_1$-$C_4$ perfluoroalkyl, $C_1$-$C_4$ alkoxy, $C_2$-$C_4$ monohydroxyalkoxy, $C_3$-$C_4$ dihydroxyalkyl and halogen; and said composition also containing at least one member selected from the group consisting of oxidation hair dyes and other direct hair dyes different from the 2,6-dinitro-aniline derivatives of formula (I).

4. A composition according to claim 3, wherein said 2,6-dinitro-aniline derivative having said formula (I) is selected from the group consisting of 2,6-dinitro-4-methyl-(2'-hydroxy-ethyl)aniline, 2,6-dinitro-4-methyl-(2',3'-dihydroxy-propyl)aniline, 2,6-dinitro-4-trifluoromethyl-(2'-hydroxy-ethyl)aniline, 2,6-dinitro-4-methoxy-(2', 3'-dihydroxy-propyl) aniline, 2,6-dinitro-4-methoxy-(2'-hydroxyethyl) aniline, 2,6-dinitro-4-(2'-hydroxy-ethyl-oxy)-(2''-hydroxy-ethyl) aniline, 2,6-dinitro-4-(2'-hydroxy-ethyl-oxy)-(2'', 3''-dihydroxy-propyl) aniline and 4-chloro-2,6-dinitro-(2',3'-dihydroxy-propyl) aniline.

5. A composition according to claim 3, which contains at least one of said other direct hair dyes.

6. A composition according to claim 5, in which said other direct hair dye is selected from the group consisting of 2-amino-4-nitro-phenol, picramic acid, 2-(2'-hydroxy-ethyl)-amino-4,6-dinitro-phenol, 1-(2'-hydroxy-ethyl)amino-2-amino-4-nitro-benzene, 4-(2'-ureido-ethyl)amino-nitro-benzene, 4-(2'30'-dihydroxy-propyl) amino-3-nitro-trifluoromethylbenzene, 4-(2'-hydroxy-ethyl) amino-3-nitro-toluene, 2-nitro-4-(2'-hydroxy-ethyl) aminoaniline, 1,4-bis(2-hydroxy-ethyl)amino-4-N-ethyl-2-nitro-benzene, 2,5bis(2'-hydroxy-ethyl)amino-nitrobenzene, 1-amino-4-(2', 3'-dihydroxy-propyl)amino-2-nitro-5-chloro benzene, 4-bis(2'-hydroxy-ethyl)amino-1-methyl-amino-2-nitro-benzene, 1-amino-2-nitro-4-bis(2'-hydroxy-ethyl)aminobenzene, Basic Violet 1 (C. I. 42 535), Acid Brown 4 (C. I. 14 805) and Disperse Violet 4 (C. I. 61 105).

7. A composition according to claim 5, which contains 1 to 5% by weight of at least one synthetic or natural polymer.

8. A composition according to claim 7, wherein said synthetic or natural polymer is a member selected from the group consisting of chitosan, polyvinyl pyrrolidone, polyvinyl acetate, polyvinyl alcohol, polyacrylic acid, polymethacrylic acid, polyacrylic nitrile, polyvinyl lactam and copolymers of these compounds.

9. A composition according to claim 3, which contains at least one of said oxidation hair dyes.

10. A composition according to claim 9, wherein said oxidation hair dye is selected from the group consisting of p-tolylene diamine, p-phenylene diamine, p-aminophenol, m-phenylene diamine, resorcinol and m-aminophenol.

11. A 2,6-dinitro-aniline derivative having the general formula (II)

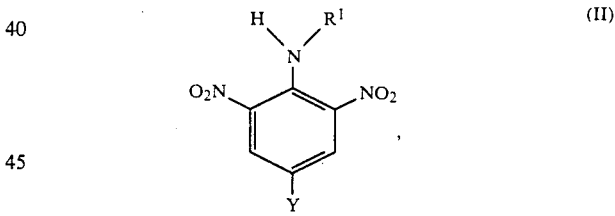

wherein $R^1$ is selected from the group consisting of $C_2$-$C_6$ monohydroxy alkyl and $C_3$-$C_4$ dihydroxy alkyl and Y is selected from the group consisting of $C_2$-$C_4$ monohydroxy alkyl, $C_1$-$C_4$ perfluoro alkyl, $C_1$-$C_4$ alkoxy, $C_2$-$C_4$ monohydroxy alkoxy, $C_3$-$C_4$ dihydroxy alkoxy and halogen, provided that, when Y represents chlorine or bromine, then $R^1$ is other than hydroxy ethyl and, when Y represents trifluoromethyl, then $R^1$ is other than monohydroxy alkyl.

12. 2,6Dinitro-4-trifluoromethyl-(2',3'-dihydroxy-propyl) aniline.

13. 2,6-Dinitro-4-methoxy-(2',3'-dihydroxy-propyl) aniline.

14. 2,6-Dinitro-4-methoxy-(2'-hydroxy-ethyl)aniline.

15. 2,6-Dinitro-4-(2'-hydroxy-ethyl-oxy)-(2''-hydroxy-ethyl) aniline.

16. 2,6-Dinitro-4-(2'-hydroxy-ethyl-oxy)-(2'',3''-dihydroxy-propyl) aniline.

17. 4-Chloro-2,6-dinitro-(2',3'-dihydroxy-propyl) aniline.

18. A composition according to claim 4, which contains at least one of said other direct hair dyes.

19. A composition according to claim 6, which contains 1 to 5 % by weight of at least one synthetic or natural polymer.

20. A composition for dyeing hair, which contains 0.01 to 2.0 percent by weight of said 2,6-dinitro-aniline derivative according to claim 11 in one of a cream, a gel, an emulsion and a solvent selected from the group consisting of water, ethanol, propanol, isopropanol and glycerol.

21. A composition according to claim 20, further containing 1 to 5% by weight of a synthetic or natural polymer selected from the group consisting of chitosan, polyvinyl pyrrolidone, polyvinyl acetate, polyvinyl alcohol, polyacrylic acid, polymethacrylic acid, polyacrylic nitrile, polyvinyl lactam and copolymers of these compounds.

22. A composition according to claim 20, further containing an oxidation hair dye selected from the group consisting of p-tolylene diamine, p-phenylene dimaine, p-aminophenol, m-phenylene dimaine, resorcinol and m-aminophenol.

23. A composition according to claim 20, further containing another direct hair dye different from said 2,6-dinitro-aniline derivative selected from the group consisting of 2-amino-4-nitrophenol, picramic acid, 2-(2'-hydroxyethyl)-amino-4,6-dinitrophenol, 1-(2'-hydroxyethyl)amino-2-amino-4-nitrobenzene, 4-(2'ureidoethyl)amino-nitrobenzene, 4-(2',3'-dihydroxypropyl)amino-3-nitrotrifluoromethyl benzene, 4-(2'-hydroxyethyl)amino-3-nitrotoluene, 2-nitro-4-(2'-hydroxyethyl)aminoaniline, 1,4-bis-(2-hydroxyethyl)amino-4-N-ethyl-2-nitrobenzene, 2,5-bis(2'-hydroxyethyl)aminonitrobenzene, 1-amino-4-(2',3'-dihydroxypropyl)amino-2-nitro-5-chlorobenzene, 4-bis(2'-hydroxyethyl)amino-1-methylamino-2-nitrobenzene, 1-amino-2-nitro-4-bis-(2'-hydroxyethyl) aminobenzene, *Basic Violet* 1 (C. I. 42 535), *Acid Brown* 4 (C. I. 14 805) and *Disperse Violet* 4 (C. I. 61 105).

* * * * *